United States Patent [19]
Thompson

[11] Patent Number: 5,961,444
[45] Date of Patent: Oct. 5, 1999

[54] IN VITRO FERTILIZATION PROCEDURE USING DIRECT VISION

[75] Inventor: Ronald J. Thompson, Ft Thomas, Ky.

[73] Assignee: Medworks Corporation, Louisville, Ky.

[21] Appl. No.: 08/953,063

[22] Filed: Oct. 17, 1997

[51] Int. Cl.[6] .......................... A61B 17/43; A61B 17/435
[52] U.S. Cl. ................................. 600/33; 600/34
[58] Field of Search ................ 600/33–35, 101, 600/115, 116, 104, 164; 604/55, 93, 96–103

[56] References Cited

U.S. PATENT DOCUMENTS

| | | | |
|---|---|---|---|
| 4,653,475 | 3/1987 | Seike et al. | 604/104 X |
| 4,654,025 | 3/1987 | Cassou et al. | 604/55 |
| 4,701,161 | 10/1987 | Lenck | 604/55 |
| 5,360,389 | 11/1994 | Chenette | 600/34 |

*Primary Examiner*—Samuel Gilbert
*Attorney, Agent, or Firm*—Don Halgren

[57] ABSTRACT

The present invention covers a method for the emplacement of an embryo against an endometrium wall of a uterus. The method comprises the steps of: placing the embryo onto a balloon; inserting the balloon into a uterus; inflating the balloon in the uterus, so as to expand the balloon and the embryo thereon against the endometrium for implantation in the uterus. The invention also includes an apparatus for the emplacement of that embryo against an endometrium wall of a uterus. The apparatus includes a balloon having an outer surface for the receipt of an embryo thereon, a hollow inserter tube having a proximal and a distal end, and an optical fiber viewing device movably arranged within the hollow inserter tube. The balloon is arranged on the distal end of the inserter tube. A cavity is arranged adjacent the distal end of the inserter tube, for receipt of a portion of the balloon during insertion of the balloon on the inserter tube into a uterus.

30 Claims, 13 Drawing Sheets

IN VITRO FERTILIZATION PROCEDURE USING DIRECT VISION

BACKGROUND OF THE INVENTION

1. Field of the Invention

This invention relates to fertilization procedures for human females, and more particularly to an apparatus and procedure for performing such procedures.

2. Prior Art

Once every 28 days or so, in the reproductive cycle of a post-pubescent human female, a single secondary oocyte (ovum) emerges from a weakened portion of the ovary wall to which it was attached, and is carried by ciliary action along the uterine tube toward the uterus, for fertilization.

This reproductive cycle for a human female is divided into the follicular phase, which is the first 14 days, and the luteal phase, which is the last 14 days of this 28 day cycle. During the follicular phase, pituitary hormones stimulate the development of one or two small cysts in the ovary, each containing an ovum. Cells surrounding the developing ovum produce estrogen that, in turn, stimulates the growth of the endometrium, the velvet-like interior lining of the uterus. On day 13, a second hormone is released from the pituitary, causing ovulation—the release of the ovum from the ovary. The distal fingers of the fallopian tube embrace the ovum and envelope it in the distal tube (the ampulla). Fertilization, the union of the ovum and the sperm, can occur only in the ampulla. After fertilization, the zygote, (the fertilized ovum), slowly migrates down the fallopian tube, and, on the sixth day post-conception, attaches to the endometrium in the uterus (implantation). Of all of the normal reproductive activities, implantation is the most poorly understood.

The luteal phase is from day 14 to day 28. After ovulation, the ovary changes functions and produces progesterone at the exact site of ovulation. The site in the ovary is yellow, and is therefore named corpus luteum, or yellow body. The action of the progesterone on the endometrium is to stop the estrogen-mediated growth of the endometrium and prepare it for the reception and support of the developing embryo. When implantation of the embryo into the endometrium occurs, the embryo divides into two distinct cell lines; the placental line and the fetal line. The placental tissue produces human chorionic gonadotrophin (HCG), which acts to continue the ovarian corpus luteum production of progesterone for twelve weeks. After twelve weeks, the placenta produces an adequate amount of progesterone to support and continue the pregnancy. The measurement of the HCG is the pregnancy test. In normal pregnancies, HCG can be detected about day 26, and doubles every two days.

The cervix is the junction of the vagina and the intrauterine cavity. It is a three centimeter canal, lined by mucous-producing cells under direct hormonal control of estrogen and progesterone. On day 13 of the cycle, the high estrogen titre causes the cervical mucous to be thin and watery and easily traversed by sperm. For the rest of the entire 28 day cycle, the cervical mucous is thick and acts as a plug and a natural barrier which prevents entrance of sperm and oxygen into the intrauterine environment.

A transvaginal ultrasound is very helpful in the monitoring of pregnancy in early stages. At five weeks from the last menstrual period (LMP), a gestational ring is easily visualized; this is placenta on the outside and ammonitic fluid inside. At six weeks from the LMP, this gestational ring is twice the size that it was at five weeks. At seven weeks from the LMP, a heartbeat is detectable with the ultrasound. Patients are reassured that there is a 99% chance of delivery once the heartbeat is seen. The heartbeat signifies a normal 46 chromosomal embryo. The lack of a heartbeat by eight weeks from the LMP denotes a miscarriage because of imperfect chromosomes of 45 or 47.

If implantation does not occur six days after fertilization, the genetics are completely abnormal and the fertilized egg did not even divide. Therefore, the HCG pregnancy test is negative, and the patient has a normally timed menstrual flow (days 25 and 28 respectively).

Fertilization is also a function of maternal age. By age fifteen, one pregnancy may occur for two cycles (two fertilizations);—at age twenty, one fertilization for three cycles (three fertilizations);—at age thirty, one pregnancy for four to five cycles (four or five fertilizations).

This principal is also reflected in the frequency of miscarriage and of Down's Syndrome (47 chromosomes), the risk of which doubles every five years from age fifteen to age forty:

| (age) 20 | 1/2000 |
|---|---|
| 30 | 1/1000 |
| 35 | 1/356 |
| 40 | 1/96 |
| 45 | 1/20 |

The relationship between maternal age and both miscarriage and Down's Syndrome is due to the genetic damage in the ova caused by gamma radiation. The cumulative dosage effect of gamma radiation causes the ova to have 22 or 24 chromosomes, rather than the normal 23.

In Vitro ("in a test tube") Fertilization (IVF) offers women who face these above-identified problems, and who have a difficulty conceiving, a means of having a successful pregnancy.

In vitro fertilization is a process of removing a mature ovum from the stimulated ovary, combining the ovum with sperm outside of the body, allowing the fertilized ovum to grow and divide, and then replacing the ovum transcervically into the uterine cavity with hopes of implantation and the establishment of a pregnancy. The primary indications of IVF are tubal disease, oligospermia, endometriosis, and unexplained infertility. The specific steps in IVF and the associated success of each step are; 1. downregulation-use of a hormone to prevent the pituitary from normal stimulatory function—100%; 2. follicular development-daily injections of FSH (follicle stimulating hormone)—100%; 3. ovum retrieval-ultrasound-guided transvaginal placement of a long needle beneath the cervix in the vagina, into the peritoneal cavity, and the sequential draining of each follicle to isolate its ovum—95%; 4. actual fertilization—combining of the ovum and processed sperm—90%; and 5. embryo transfer—after fertilization has occurred, the zygotes are allowed to grow and divide for 24, 48, or 72 hours. The embryos then are withdrawn into a thin plastic tube, and the tube is used to penetrate the endocervical canal, and the embryos are injected into the intrauterine cavity. These embryos are free floating and must attach the endometrium and implant in order for the procedure to result in a pregnancy. Usually four or five embryos are transferred into the intrauterine cavity; however, even under optimal conditions, the success rate is 33% at best. The low success rate of this IVF approach is directly related to embryo transfer and poor implantation rate. The possible causes for the poor implantation rate are: 1. free floating embryos and the lack of a sustained juxtaposition of the embryo against the endometrium; 2. high $O_2$ tension because of the transcervical embryo transfer and introduction of room air (21% $O_2$) into a normally $CO_2$ environment; 3. antibody/antigen interactions—the initial implantation has been postulated as a positive/negative electrical attraction-interaction between the embryo and the endometrium. A continuing juxtaposition of the embryo and the endometrium might allow implantation and factor out electrical interactions.

This type of IVF procedure can have many complications. Because of the low implantation rate per embryo, usually four or five embryos are transferred into the intrauterine cavity in hopes that one will implant. In 30% of the successful IVF cycles, twins will be produced; in 10% of IVF cycles, four to five embryos will implant. If the implantation rate could be improved, fewer embryos would have to be transferred, and the percentage of multiple births could be reduced or even eliminated.

During this embryo transfer of this procedure, pressure is applied to a syringe to expel the embryos from the tip of the transfer catheter into the intrauterine cavity. This pressure is subject to variation, and at times may push the embryos into the proximal fallopian tubes. A tubal or ectopic pregnancy will not continue as a normal pregnancy, and usually requires a surgical removal of the ectopic pregnancy. The ectopic rate for IVF is reported as two to five percent.

It is an object of the present invention to overcome the disadvantages of the prior art.

It is a further object of the present invention, to provide an apparatus and procedure which will permit a direct vision embryo transfer utilizing an intrauterine retention balloon for IVF.

BRIEF SUMMARY OF THE INVENTION

The present invention provides a method and apparatus to transfer preferably just one or two embryos under direct vision using micro fiberoptic technology into a woman's uterus. This procedure would allow the precise placement of the embryo in the optimum location in the uterus, by juxtaposing the embryo against the velvety endometrium using a pressurized balloon, and maintain the application of that embryo thereagainst, for a period of days to increase the success rate of implantation. A pressure-regulating valve on the proximal end of the balloon will prevent over inflation of that balloon initially, and also permit a reduction of volume in the balloon as the pregnancy grows into the space of the intrauterine cavity. The pressurized balloon will also permit the occlusion of the endocervix to prevent the egress of oxygen into the intrauterine environment in which the attempted implantation is occurring.

The embryo transfer apparatus has two configurations. The first configuration relates to the loading of an embryo into the apparatus and transvaginally, transcervically placing the embryo in the proper position in the intrauterine cavity against the endometrium. In the second configuration, the balloon is inflated to hold the embryo against the endometrium for implantation thereon, and initiation of the pregnancy. The balloon may remain in position for 3–10 days, depending on results from clinical studies.

Embryo loading and actual intrauterine insertion would depend on a semi-rigid tubular inserter. The inserter would have a hollow center to accommodate the fiber optic microendoscopy/insufflation technology (either rigid or flexible). The distal tip of the inserter is preferably rounded, and is splitable, for eventual protrusion of the fiber optic lens therepast, but which distal tip would withstand the pressure of transcervical placement. An opening is arranged about one centimeter back from the distal tip of the inserter, and is fitted with a pocket formed from the invagination of the overlying balloon. This pocket would receive the embryo for transfer. The balloon would be semi-adherent both at the tip of the inserter and within the pocket for embryo transfer. The balloon itself is arranged to overlap the pocket, to also act as a flap valve, much like the cap of a mushroom hangs over its stem. During loading of an embryo into the inserter, the flap valve would be lifted, the embryo placed in the pocket reservoir defined by the opening at the distal end of the inserter, (which opening is balloon lined), and the flap valve replaced. The inserter would have a discharge port disposed on a distal end, preferably between the embryo retention reservoir and the distal tip of the fiber optic insuflation system. This would allow for inflation of the body of the balloon itself before the pressure would force that portion of the balloon (and embryo) within the "pocket" of the inserter therefrom, and place the embryo reservoir against the endometrium. This top-to-bottom inflation of the balloon would also expel any trapped oxygen in the intrauterine cavity.

The shaft of the inserter has a smooth surface, and has an interface with a gas tight rubber stopper at the proximal stem of the balloon outside of the exocervix. The pocket reservoir is preferably arranged one centimeter from the distal tip of the inserter for the transfer of the embryo, thus permitting, when aligned top to bottom, placement of the embryo carried therewithin, in the posterior uterine fundus, the optimum position for implantation.

The actual retention balloon would be soft, flexible, nonembryo-toxic, gas impermeable, and have a telfa-like external composition to prevent the embryo from implanting onto the balloon. Once inflated to a specific pressure, the pocket reservoir for embryo transfer would become flat to hold the embryo against the endometrium. The balloon in its inflated state would be triangular shaped to match the internal dimensions of the intrauterine cavity. The stem of the balloon would be two to four centimeters long to fit the endocervical canal; round and tubular, to accommodate the inserter and terminate with a gas-tight rubber seal outside of the cervix. This gas-tight seal would have a two centimeter diameter to further act to obstruct the cervical canal at the exocervix. The rubber seal would be fitted with a balloon pressure-regulating pop-off valve so that the balloon could not be over inflated. The pop-off valve would also allow the volume of gas within the intrauterine to be reduced as the pregnancy enlarges and increasingly occupies the intrauterine cavity.

At least two distinctly different sizes of balloons may be needed, possibly more, depending on the woman involved with this procedure. Nulliparous (no prior children) women have an elongated endovervical canal and relatively small intrauterine cavity, while parous (after one child delivered) women have a shortened endocervical canal and a larger intrauterine cavity. A hysterosalpingogram (HSG) is an X-ray where the endocervical canal and the intrauterine cavity are filled with a radio-opaque dye. At a measured pressure of the dye, the actual sizes of each can be measured pre-IVF cycle for each patient for optimum balloon fit in the intrauterine cavity.

In the practice of this procedure, the sterile assembled balloon/inserter is removed from its package. The fiber optic distal end of the video microendoscopy system is threaded through the proximal end of the inserter up to a distal stop. With sterile technique the flap valve is elevated and one or two 48–72 hour embryos are deposited into the pocket reservoir in the distal shaft of the inserter. The flap valve is replaced. The distal end of the balloon/inserter assembly is placed transvaginally until the distal end interfaces with the distal aspect of the intrauterine cavity at the fundus. Attention must be paid to upside and downside positions of the flap valve overlying the pocket reservoir containing the embryo in the posterior aspect of the fundus. $CO_2$ gas is used to slowly inflate the balloon via the microendoscopy system. Sequentially the balloon occludes the intrauterine cavity, and then, without further distension, the pocket reservoir slowly inverts to juxtapose the embryo or embryos against the endometrium. The inserter becomes a sleeve of the video microendoscope and is slowly withdrawn over the microendoscope to yield a transballoon view of the internal aspect of the endometrium and the stabilized embryo or embryos. The microendoscope and sleeve are withdrawn through the stem of the balloon and through the gas-tight seal at the exocervix. The pop-off waste gate regulates the pressure within the intrauterine balloon both initially and throughout the duration of its function within the uterus. Subsequent video microendoscope visualization of the developing implanted embryo could be accomplished five or seven days post embryo transfer through the same gas-tight rubber seal.

The invention thus comprises a method for the emplacement of an embryo against an endometrium wall of a uterus, comprising the steps of: placing the embryo onto a balloon; inserting the balloon into a uterus; inflating the balloon in the uterus, so as to expand the balloon and the embryo thereon against the endometrium for implantation thereat. The method includes the steps of: inserting the balloon over a hollow inserter tube, and directing a gas through the hollow inserter tube to inflate the balloon; arranging a pocket in the inserter tube; and emplacing a portion of the balloon in the pocket; placing an embryo on the balloon in the pocket in the inserter tube; and folding a portion of the balloon over the pocket in the inserter tube, to permit the folded portion of the balloon to act as a flap valve, keeping the embryo safe within the pocket until inflation of the balloon effects displacement of the balloon and embryo from the pocket and against the endometrium wall of the uterus. The method includes the steps of: placing a fiber optic device through the inserter tube, to permit visualization of the balloon therethrough; placing an opening in a wall portion of the tube adjacent a distal end thereof, to permit the balloon to be inflated by gas pressure from the proximal end tube; viewing the balloon and the embryo implanted against the endometrium; arranging a valve in a stem portion of the balloon to regulate the pressure of gas within the balloon; and occluding the entry of an undesired gas into the uterus by inflation of the balloon therewithin.

The invention also includes a method for the visualization of an embryo at an implantation site in a uterus, comprising the steps of: placing the embryo onto a balloon; directing a fiberoptic device into the balloon; inserting the balloon into a uterus; inflating the balloon in the uterus, so as to expand the balloon and the embryo thereon against the endometrium for implantation in the uterus; viewing the embryo through the fiberoptic device; placing the fiberoptic device into a tubular inserter; and inserting the balloon into the uterus by the tubular inserter; removing the tubular inserter to permit extended time pressurization of the balloon against the endometrium of the uterus; placing a valve in a stem of the balloon to control the pressure within the balloon as the embryo grows.

The invention also includes a method for the placement of an embryo at an optimal implantation site in a uterus, comprising the steps of: placing the embryo onto a balloon; inserting the balloon into a uterus; and inflating the balloon in the uterus, so as to expand said balloon with the embryo thereon against the endometrium for optimal implantation thereat to prevent a tubal positioning of the embryo. The method includes the steps of: placing a fiberoptic device into the balloon; and viewing the embryo through the fiberoptic device; deflating the balloon as the embryo grows within the uterus.

The invention also includes a method to regulate multiple gestations within a uterus of a human female comprising the steps of: placing an embryo onto a balloon; inserting the balloon with the embryo thereon into a uterus; and inflating the balloon in the uterus, so as to expand the balloon with the embryo thereon against the endometrium for optimal implantation of the embryo thereat and to prevent emplacement of multiple embryos onto the endometrium of the uterus. The method includes the steps of: inserting the balloon over a hollow inserter tube; directing a gas through the hollow inserter tube to inflate the balloon; arranging a pocket in the inserter tube; emplacing a portion of the balloon in the pocket; placing an embryo on the balloon in the pocket in the inserter tube; placing a fiber optic device through the inserter tube, to permit visualization of the balloon and embryo therethrough; and placing an opening in a wall portion of the tube adjacent a distal end thereof, to permit the balloon to be inflated by gas pressure from the tube.

The invention also includes an apparatus for the emplacement of an embryo against an endometrium wall of a uterus, the apparatus comprising: a balloon having an outer surface for the receipt of an embryo thereon; a hollow inserter tube having a proximal and a distal end; an optical fiber viewing device movably arranged within the hollow inserter tube; the balloon arranged on the distal end of the inserter tube; and a cavity arranged adjacent the distal end of the inserter tube, for receipt of a portion of the balloon during insertion of the balloon on the inserter tube into a uterus. The apparatus includes an inflation conduit within the inserter tube to permit inflation of the balloon inside a uterus, a flap valve arranged over the cavity holding the embryo, to permit safe delivery of the embryo in the cavity during insertion of the inserter tube, the balloon and the embryo into the uterus. The apparatus includes a regulator valve at a proximal stem end of the balloon to permit regulation of pressure of gas within the balloon during implantation of the embryo onto the endometrium in the uterus., and a frangible means arranged on the distal end of the inserter tube, to permit the optical fiber viewing device to be pushed therepast, to permit the viewing device to view the balloon and the embryo after the balloon has been inflated, and the embryo has been implanted onto the endometrium wall of the uterus.

BRIEF DESCRIPTION OF THE DRAWINGS

The objects and advantages of the present invention will become more apparent when viewed in conjunction with the following drawings, in which.

DESCRIPTION OF THE PREFERRED EMBODIMENTS

Figure 1:
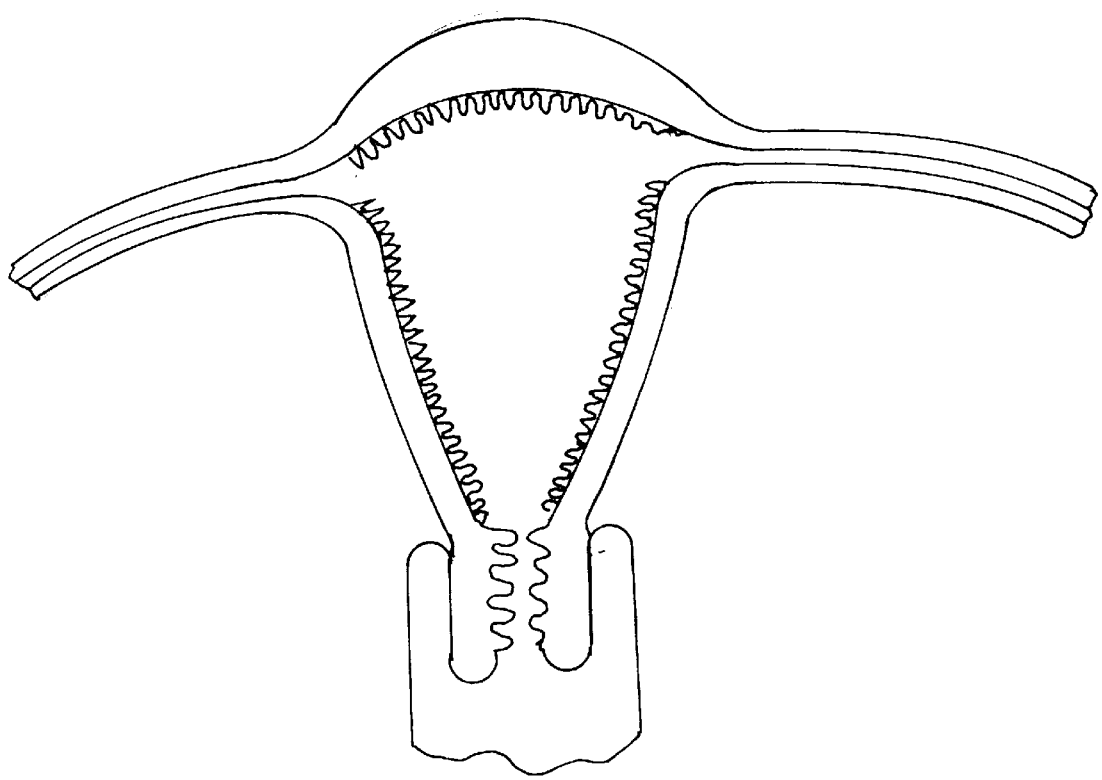
FIG. 1 is a pictorial representation of the reproductive system of a human female.
Figure 2:
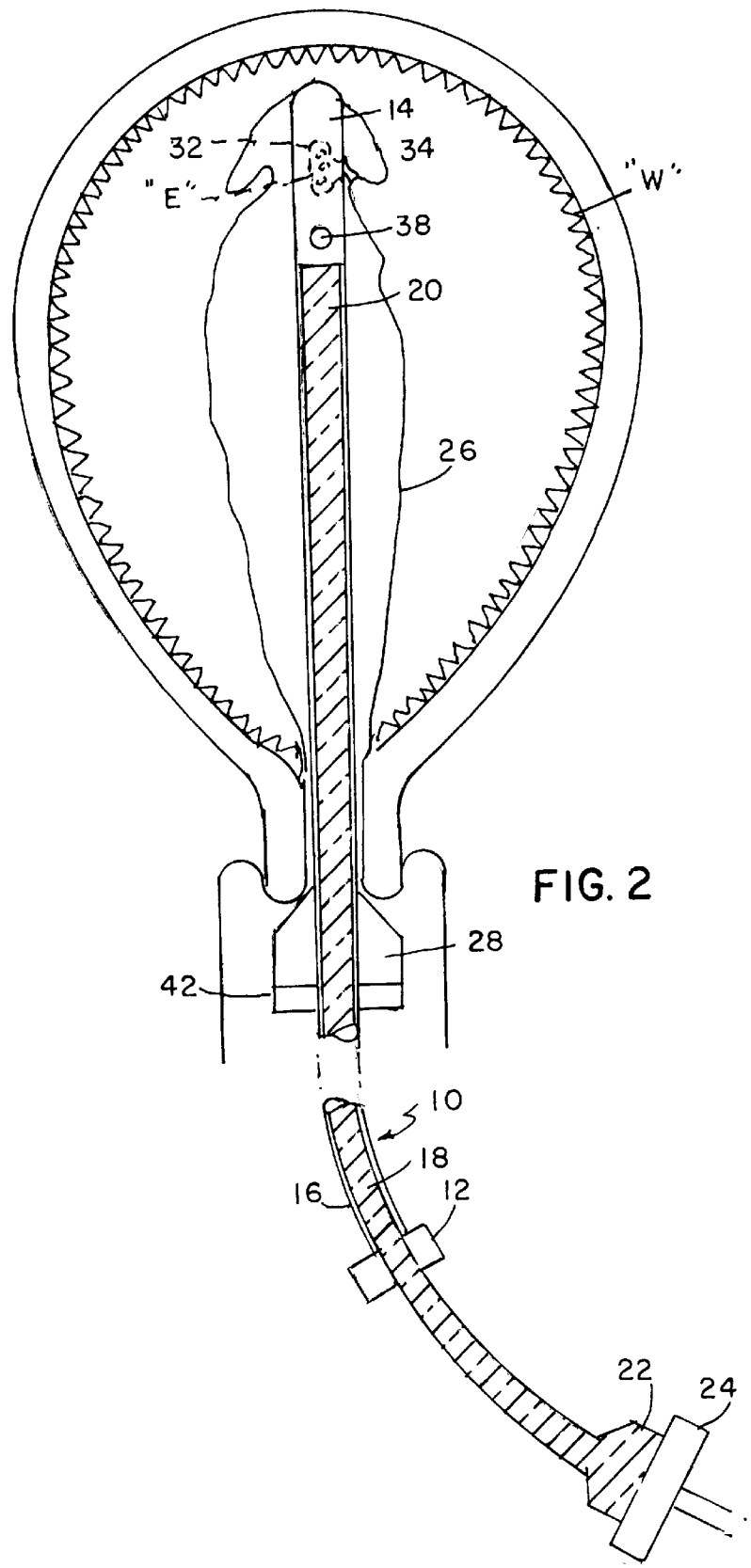
FIG. 2 is an elevational view, partly in section, of an inserter apparatus, shown in the uterus.
Figure 3:
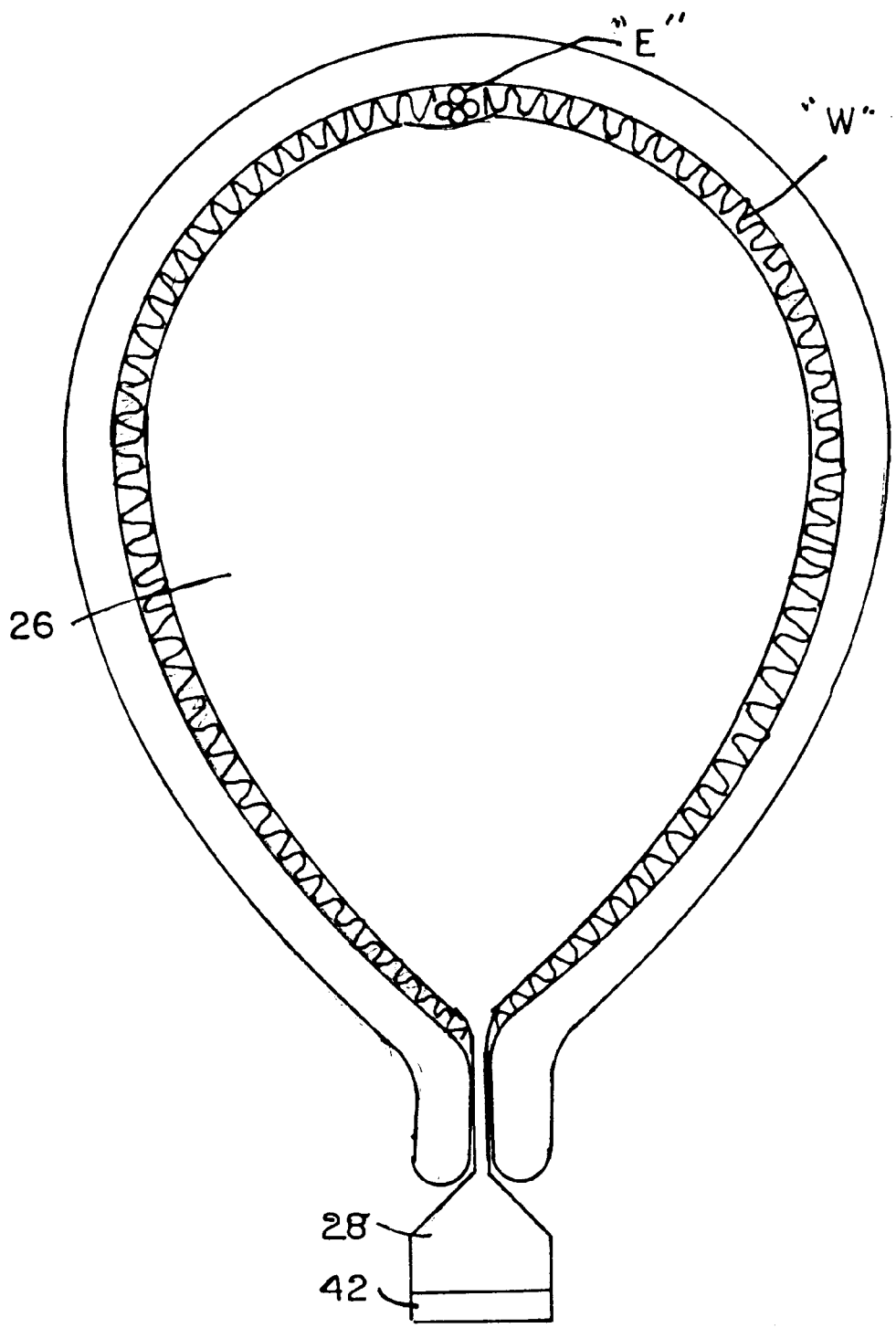
FIG. 3 is a representation of the implantation balloon of the inserter apparatus within the uterus.
Figure 12:
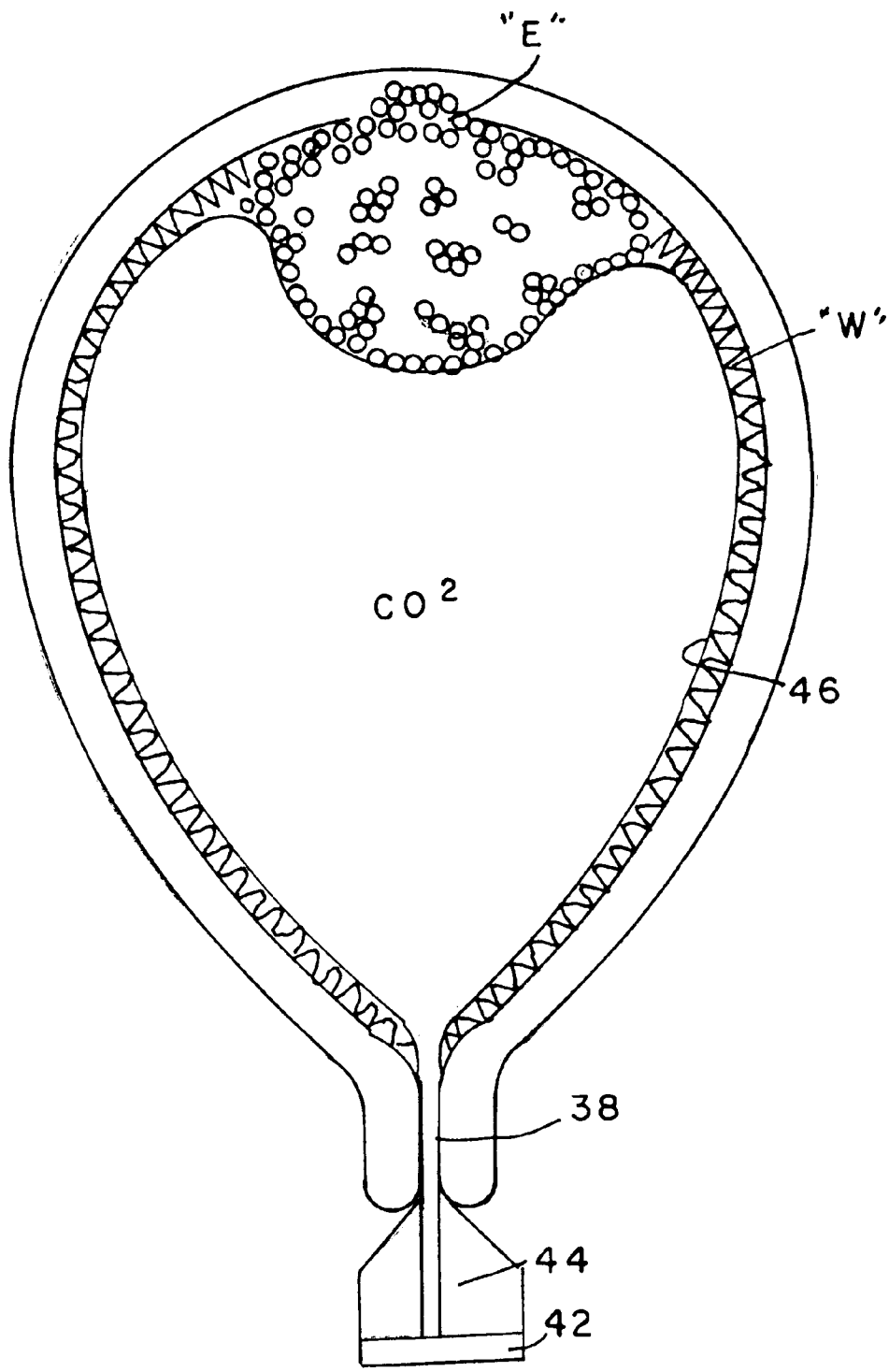
FIG. 12 is a view similar to FIG. 11, showing the embryo at a four day time from implantation.
Figure 13:
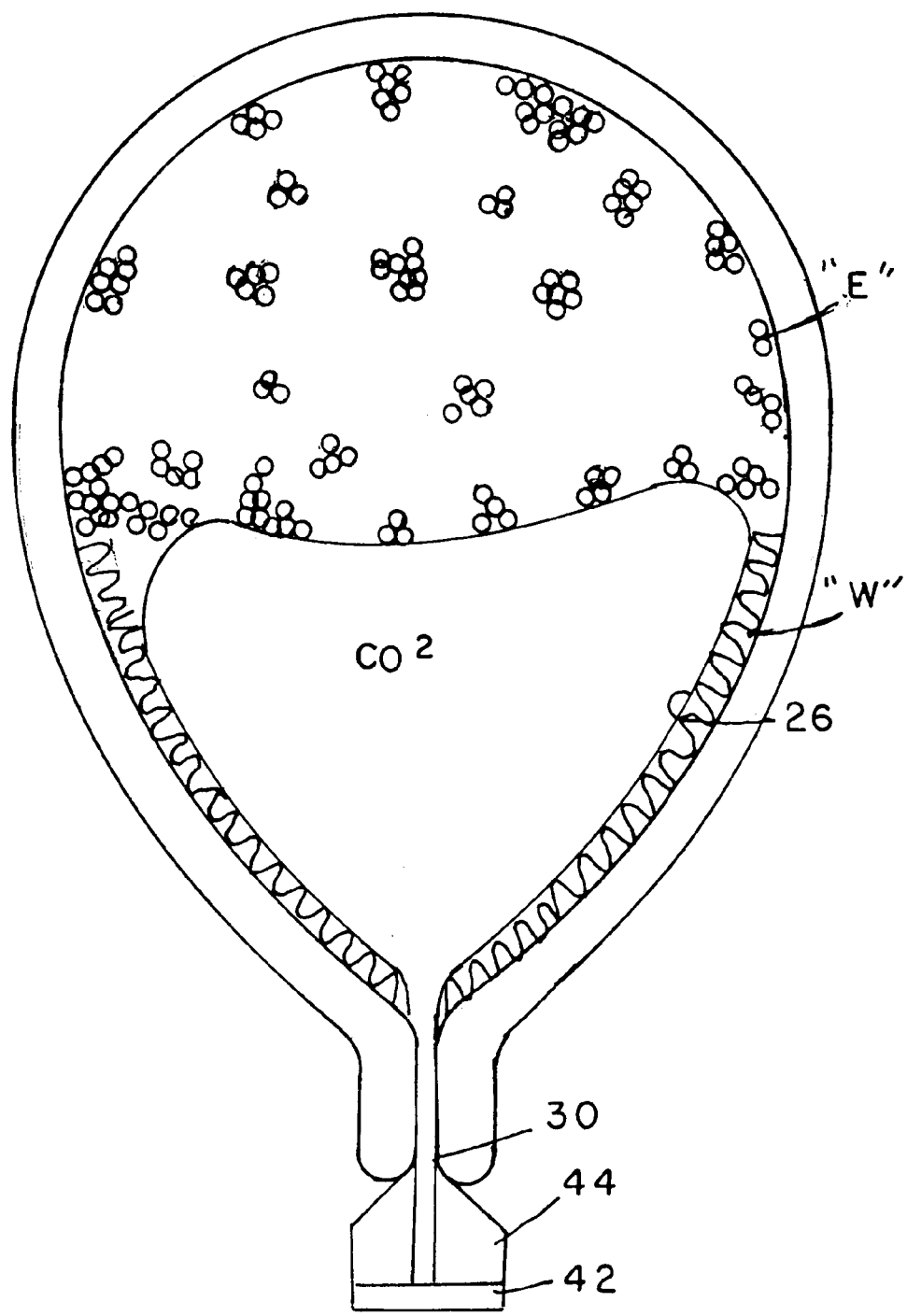
FIG. 13 is a view similar to FIG. 12, showing the embryo at a six day time from implantation.

Referring now to the drawings in detail, and particularly to FIG. 1, there is shown a representation of a female reproductive system. The present invention provides a method and apparatus 10, as shown in FIG. 2, to transfer preferably just one or two embryos under direct vision using micro fiberoptic technology into such a uterus of the female reproductive system. The transfer apparatus 10 comprises a hollow tubular inserter 12 having a distal end 14 and a proximal end 16. A fiberoptic microendoscope 18 is arranged through the tubular inserter 12. The endoscope 18 has a distal end 20 arranged near the distal end 14 of the inserter 12, and a proximal end 22, which may be fitted with a viewing eyepiece or camera 24 or the like, as shown in FIG. 2. An inflatable balloon 26 is arranged over the distal end of the inserter 12, the balloon 26 having a valved and sealable proximal end or stem 28, which extends just beyond the exocervix of the female reproductive system, as shown in FIGS. 3, 12 and 13.

Figure 4:
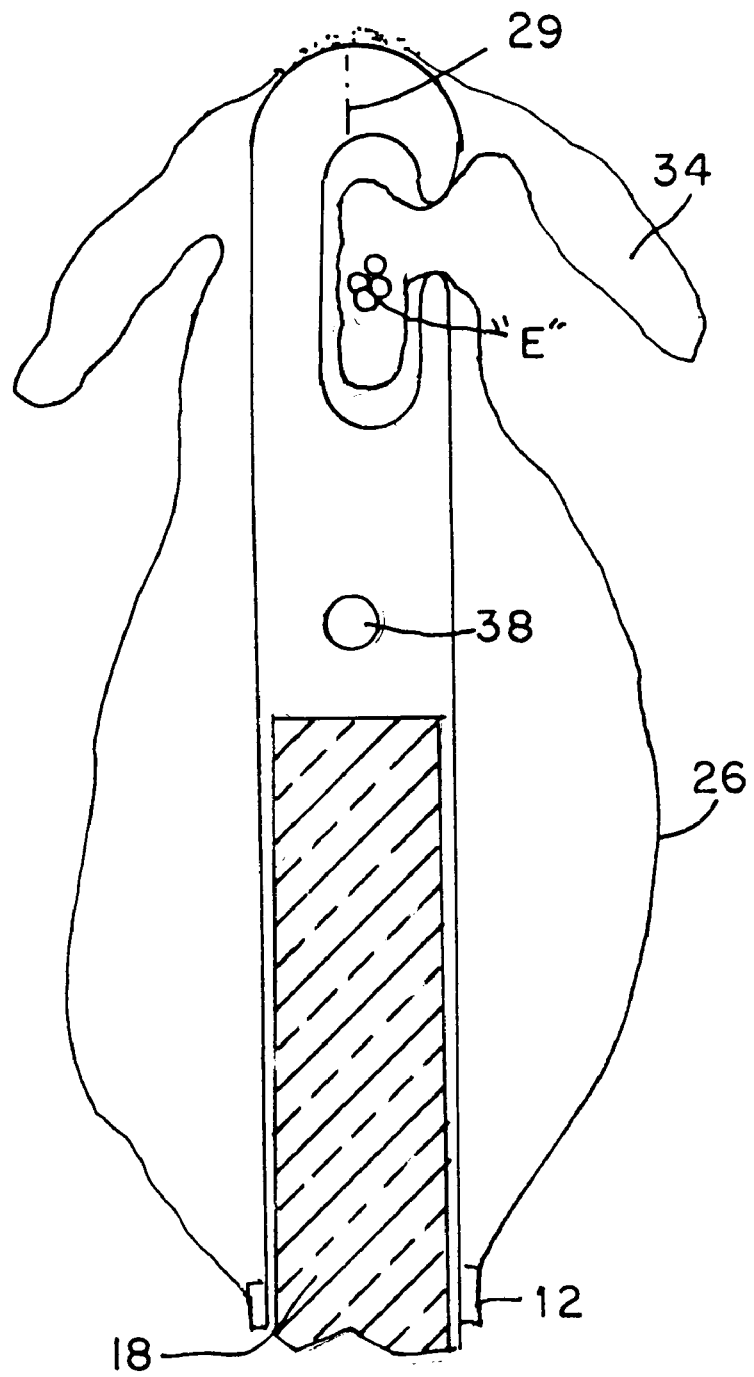
FIG. 4 is an elevational view of the distal tip of an inserter apparatus and balloon therewith.

The embryo transfer apparatus 10 has two configurations. The first configuration relates to the loading of an embryo "E" into the apparatus 10, in the uninflated state of the balloon 26, as shown in FIGS. 2 and 4, and transvaginally, transcervically placing the embryo in the proper position in the intrauterine cavity against the endometrium wall "W", as may be seen in FIG. 8. In the second configuration, the balloon 26 is inflated to hold the embryo "E" against the endometrium "W" for implantation thereon, and initiation of the pregnancy. The balloon 26 may remain in position in various stages of inflation, for 3–10 days, depending on results from clinical studies of the female being implanted.

Embryo loading and actual intrauterine insertion depends on the semi-rigid tubular inserter 12. The inserter 12 has a hollow center to accommodate the fiber optic microendoscope 18 and insufflation means at its proximal end, not shown for clarity, for inflating the balloon. The distal tip of the inserter 14, is preferably rounded, as shown in FIGS. 4, 5, 6 and 7, and has a fracture line 29, shown in FIGS. 5, 6 and 7 which line 29 is splitable, to permit eventual protrusion of the distal end 20 of the endoscope 18 with its fiber-optic lens therepast.

Figure 5:
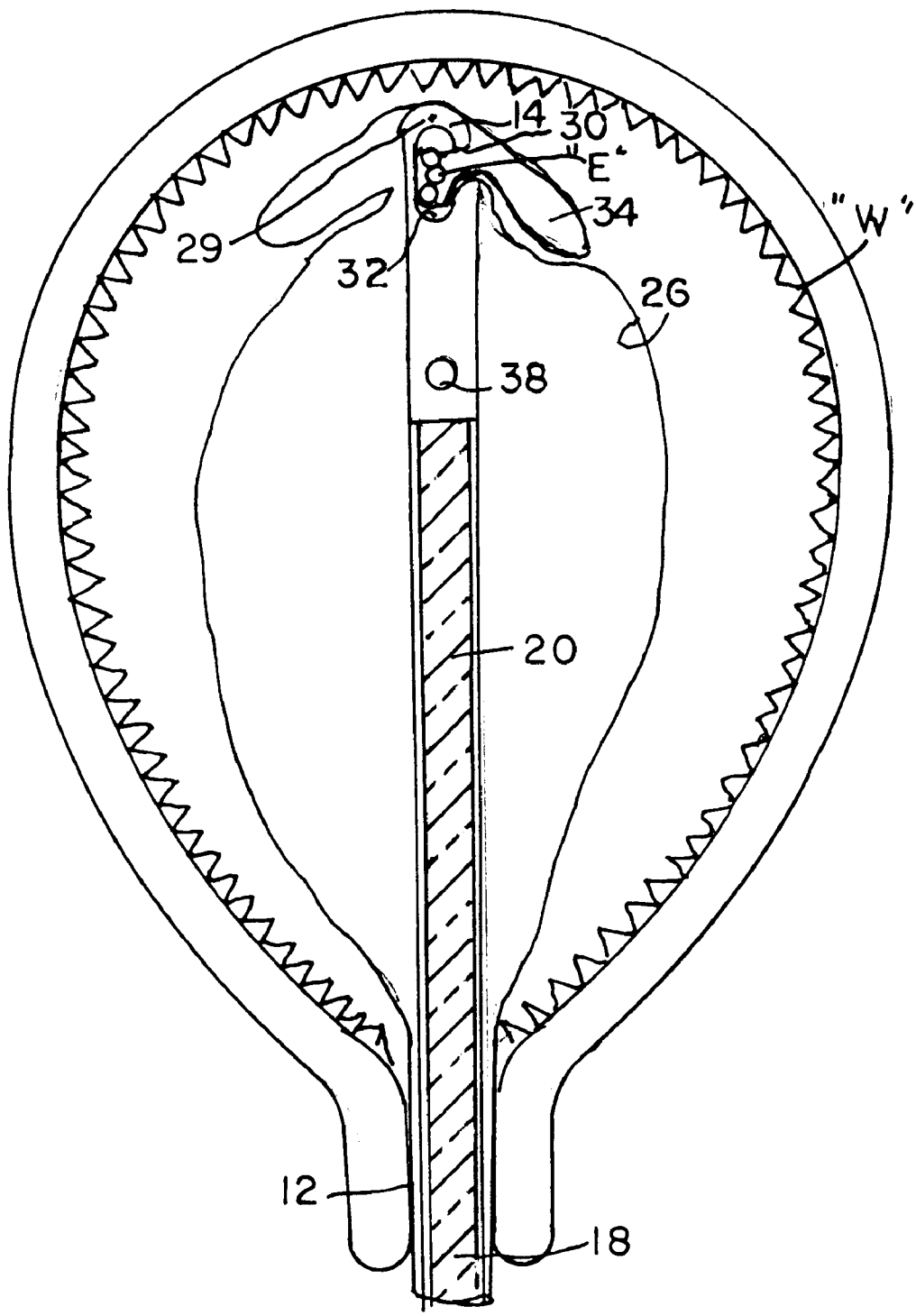
FIG. 5 is an elevational view similar to FIG. 4, showing the balloon partly expanded in a uterus.
Figure 6:
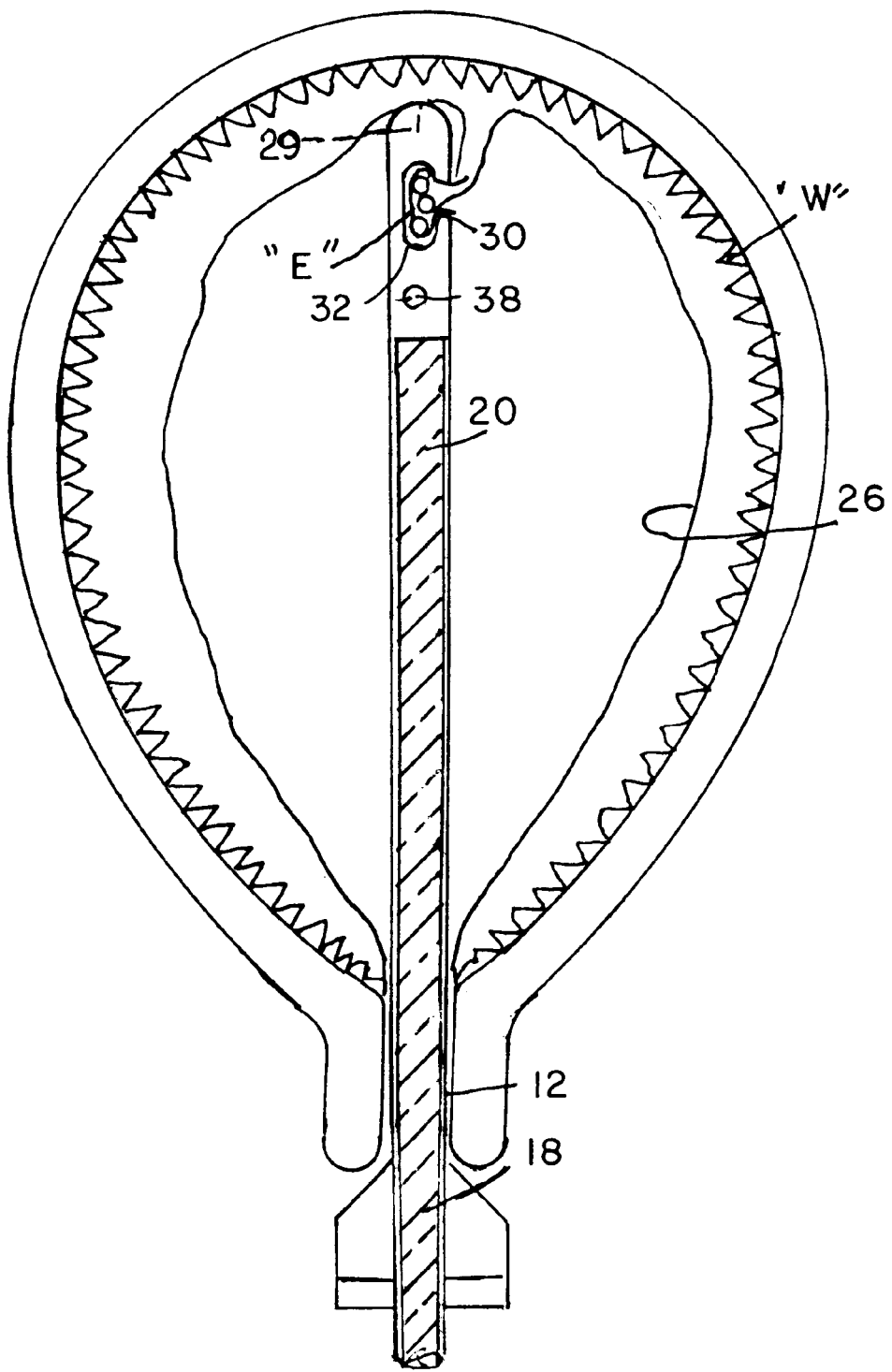
FIG. 6 is an elevational view similar to FIG. 5, showing the balloon slightly more expanded within the uterus.
Figure 8:
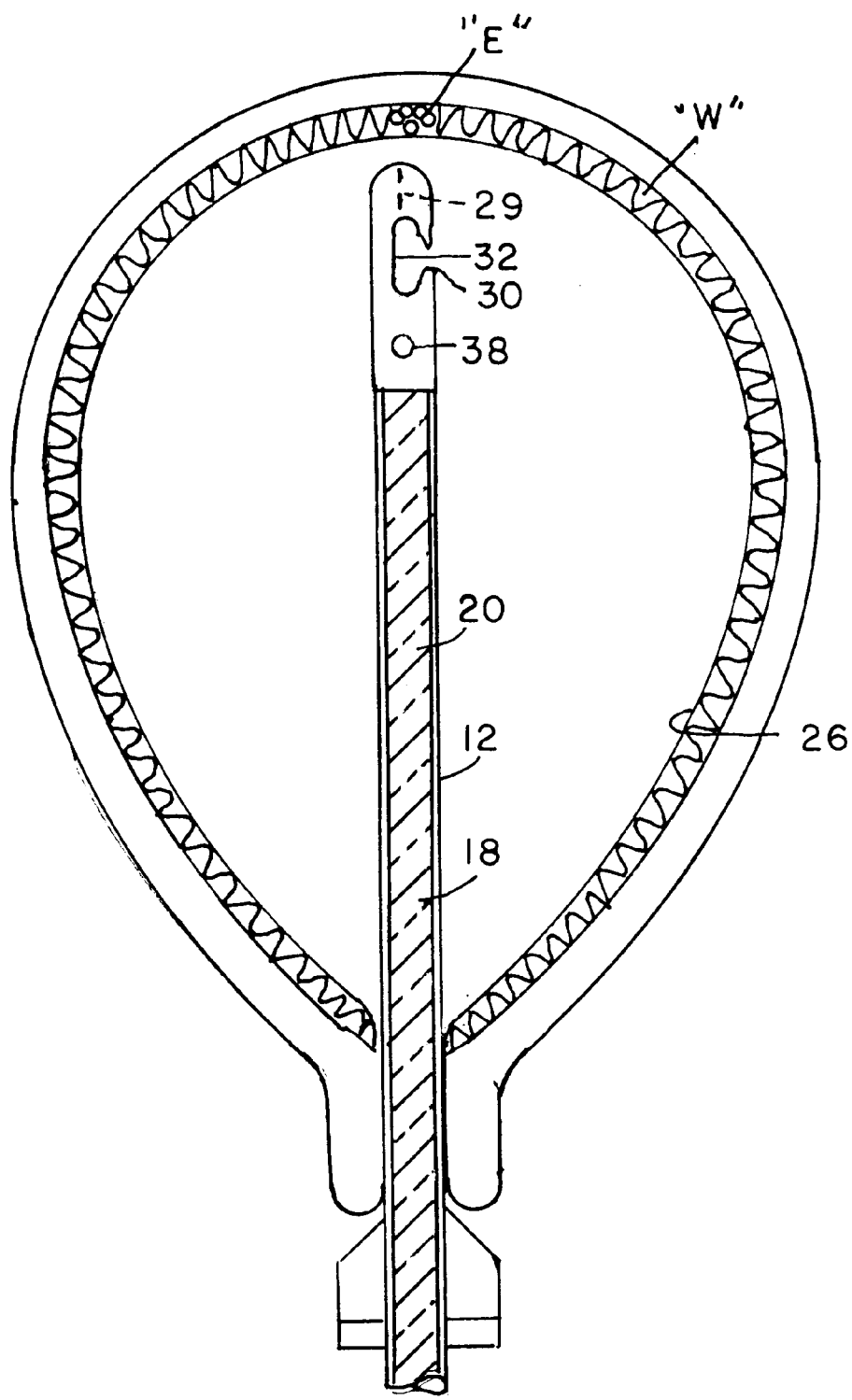
FIG. 8 is an elevational view of the balloon in full inflation within the uterus.

An opening 30 is arranged about one centimeter back from the distal tip 14 of the inserter 12, and is fitted with a pocket 32 formed from the invagination of the overlying balloon 26. This pocket 32 would receive the embryo "E" for transfer. The balloon 26 would be semi-adherent both at the tip of the inserter 12 and within the pocket 32 for embryo transfer. The balloon 26 itself is arranged to overlap the pocket 32, to also act as a flap valve 34, as shown in FIGS. 2, 4 and 5. During loading of an embryo "E" into the inserter 12, the flap valve 34 would be lifted, the embryo "E" placed in the pocket 32 reservoir defined by the opening 30 at the distal end 14 of the inserter 12, (which opening is balloon lined), and the flap valve 34 replaced over the opening 30. The inserter 12 would have a discharge port 38 disposed adjacent its distal end 14, preferably between the embryo retention reservoir (pocket) 32 and the distal tip 20 of the fiber optic endoscope 18 and its associated insufflation system. This would allow for inflation of the body of the balloon 26 itself, as shown in FIGS. 5 and 6, before the pressure would force that portion of the balloon (and embryo) within the "pocket" of the inserter therefrom, and place the embryo reservoir against the endometrium, as shown in FIG. 8. This top-to-bottom inflation of the balloon would also expel any trapped oxygen in the intrauterine cavity.

Figure 9:
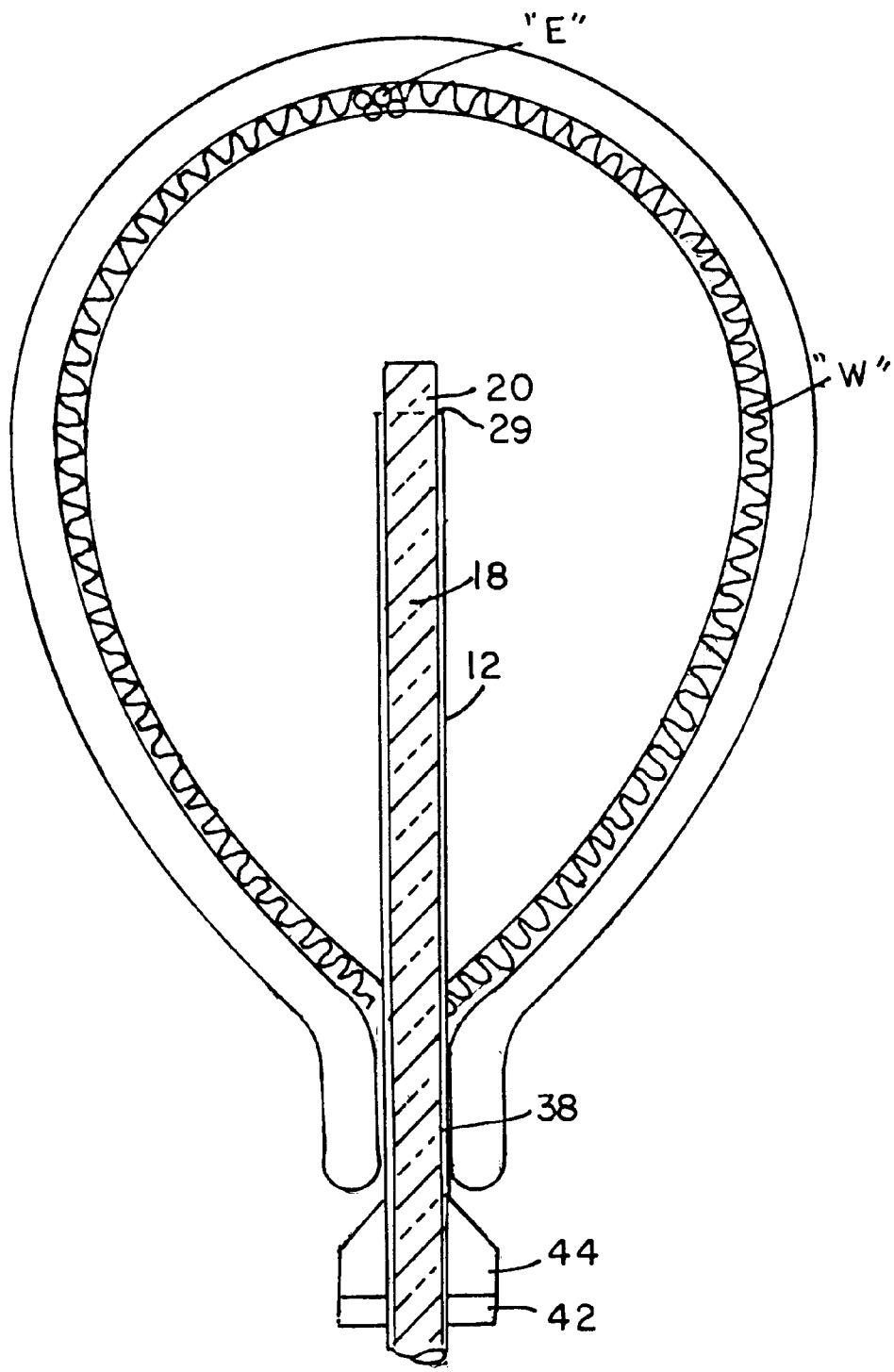
FIG. 9 is an elevational view of the full balloon in the uterus, with the embryo in place and an optical device set up for viewing such embryo.
Figure 10:
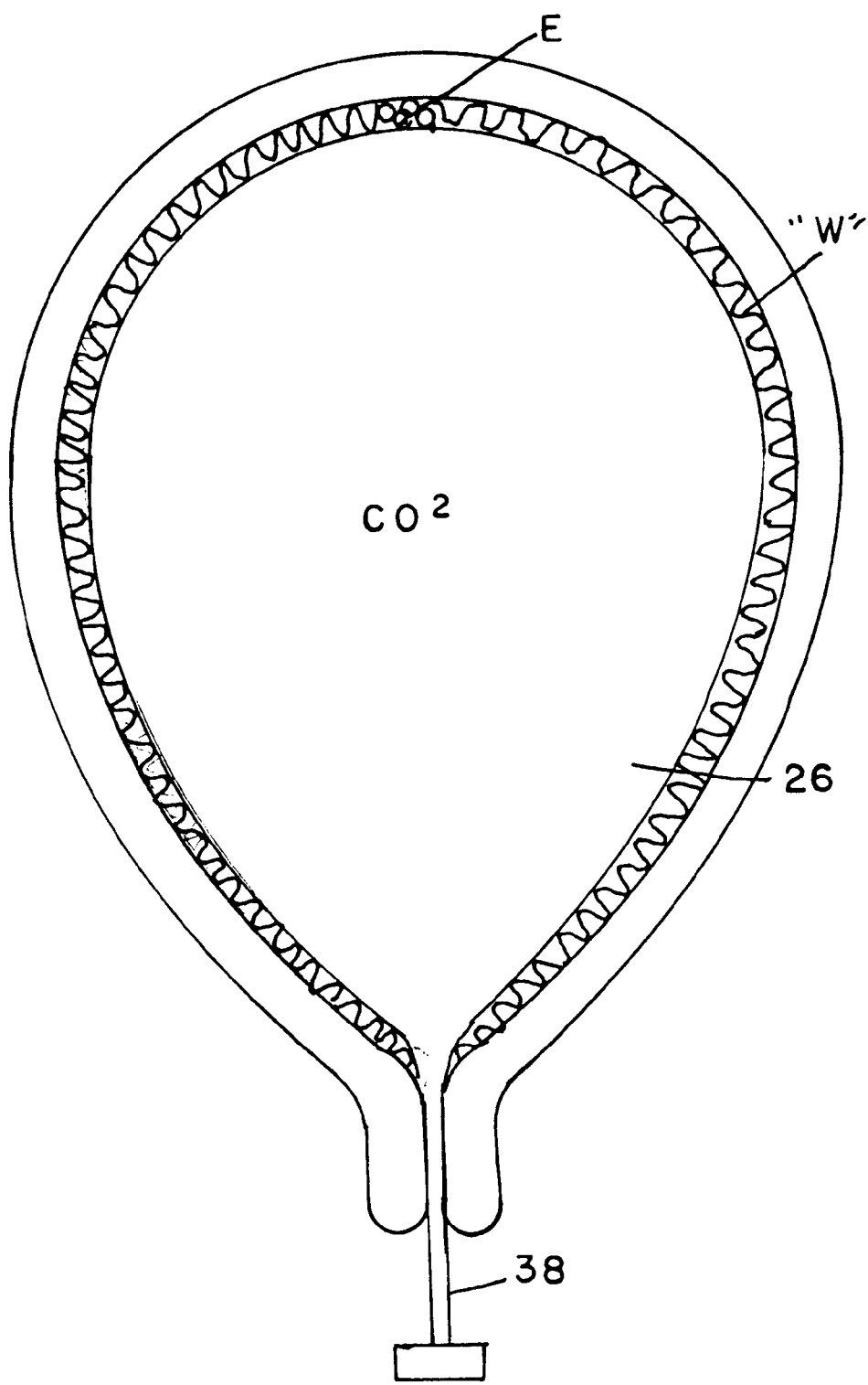
FIG. 10 is an elevational view of the fully inflated balloon in the uterus, without any optical device therewithin.

The shaft of the inserter 12 has a smooth surface, and has an interface with a gas tight rubber stopper 42 at the proximal stem 28 of the balloon 26 outside of the exocervix, as shown in FIG. 9. The pocket reservoir 32 is preferably arranged one centimeter from the distal tip 14 of the inserter 12 for the transfer of the embryo "E", thus permitting, when aligned top to bottom, placement of the embryo "E" carried therewithin, in the posterior uterine fundus, the optimum position for implantation, as shown in FIGS. 3, 9, and 10.

Figure 11:
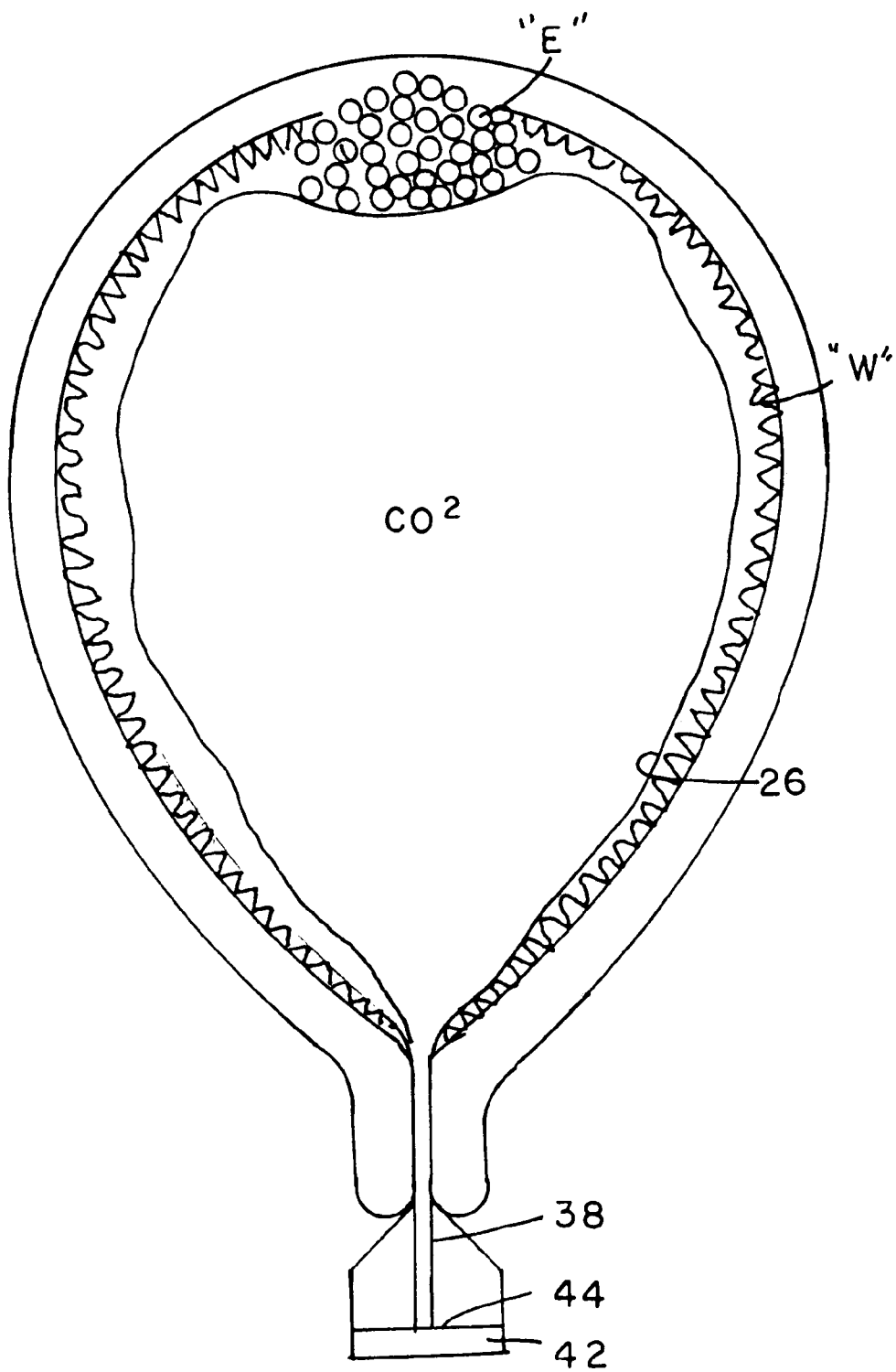
FIG. 11 is an elevational view of the uterus showing the embryo at a two day implantation time in the uterus.

The actual retention balloon 26, would be soft, flexible, nonembryo-toxic, gas impermeable, and have a telfa-like external composition to prevent the embryo from implanting onto the balloon. Once inflated to a specific pressure, the reservoir pocket 26 for embryo transfer would become generally flat, as shown in FIG. 3, to hold the embryo against the endometrium. The balloon 26 in its inflated state would be triangular shaped to match the internal dimensions of the intrauterine cavity. The stem 28 of the balloon 26 would be two to four centimeters long to fit the endocervical canal; round and tubular, to accommodate the inserter and terminate with a gas-tight rubber seal outside of the cervix. This gas-tight seal has a two centimeter diameter to further act to obstruct the cervical canal at the exocervix. The rubber seal would be fitted with a balloon pressure-regulating pop-off valve 44, so that the balloon 26 could not be over inflated. The pop-off valve 44 would also allow the volume of gas within the balloon 26 in the intrauterine cavity to be reduced as the pregnancy enlarges and increasingly occupies the intrauterine cavity, as represented in FIGS. 11, 12 and 13.

Figure 7:
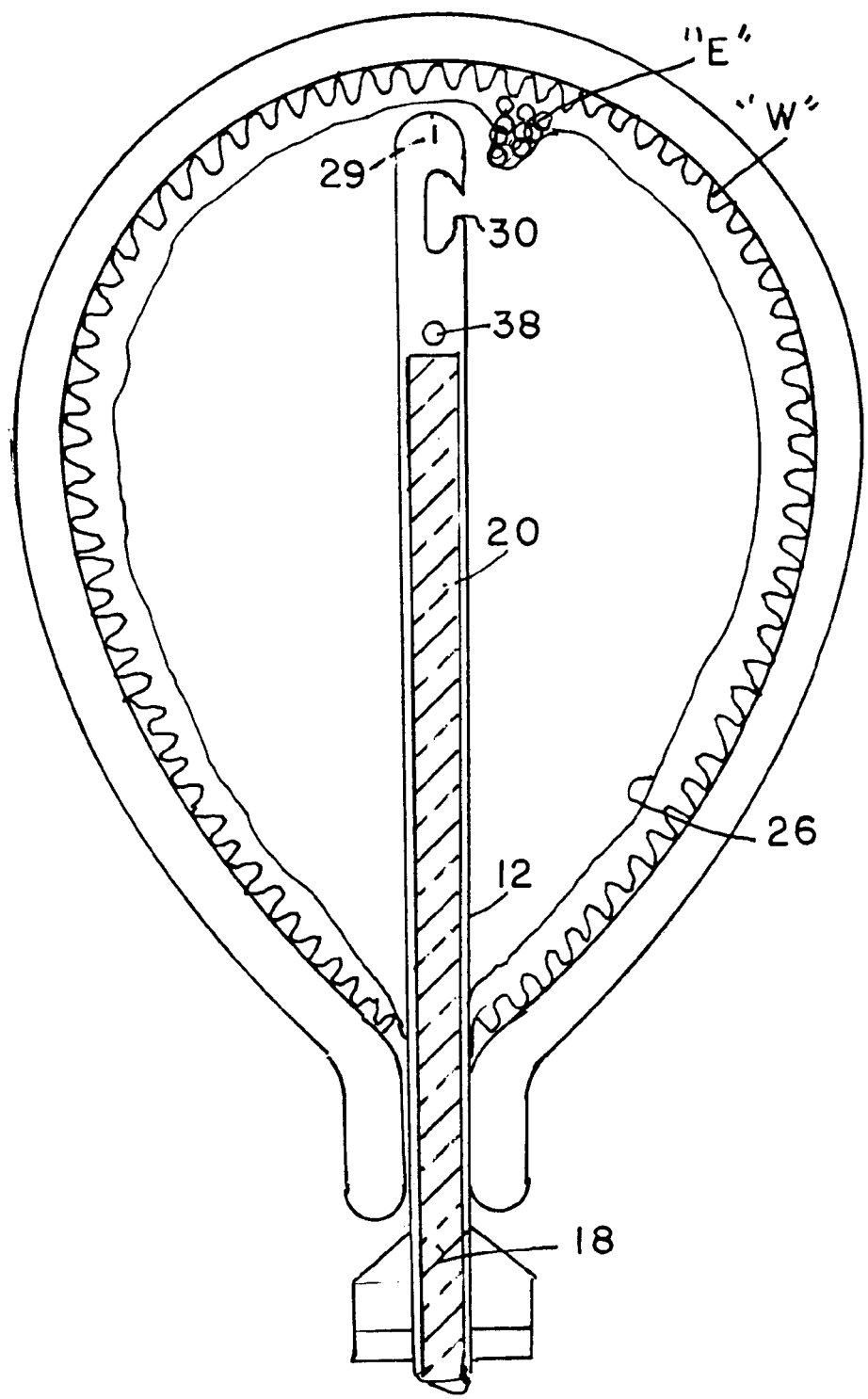
FIG. 7 is an elevational view similar to FIG. 6, showing the balloon near full inflation.

In the practice of this procedure, the sterile assembled balloon/inserter apparatus 10 is removed from its package, not shown. The fiber optic distal end 20 of the video microendoscope 18 is threaded through the proximal end 14 of the inserter 12 up to a distal stop. With sterile technique, the flap valve 34 is elevated and one or two 48–72 hour embryos "E" are deposited into the reservoir pocket 32 in the distal end shaft of the inserter 12. The flap valve 34 is replaced. The distal end of the balloon/inserter assembly 10 is placed transvaginally until the distal end interfaces with the distal aspect of the intrauterine cavity at the fundus. Attention must be paid to upside and downside positions of the flap valve 34 overlying the reservoir pocket 32 containing the embryo "E" in the posterior aspect of the fundus. $CO_2$ gas is used to slowly inflate the balloon 26 via the lumen in the microendoscopy system 18$m$ in the inserter 12. Sequentially the balloon 26 inflates, it occludes the intrauterine cavity, as shown in FIG. 5, and then, without further distension, the reservoir pocket 32 slowly inverts, as shown in FIGS. 6 and 7, to juxtapose the embryo or embryos "E"

against the endometrium "W" as shown in FIG. 8, the balloon 26 being basically fully inflated. The inserter 12 becomes a sleeve of the video microendoscope 18, the inserter 12 being slowly withdrawn over the microendoscope 18, as shown in FIG. 9, the fracture line 29 having split, to permit a transballoon view of the internal aspect of the endometrium and the stabilized embryo or embryos "E". The microendoscope 18 and inserter 12 are withdrawn through the stem of the balloon 26, and through the gas-tight seal at the exocervix, leaving the inflated balloon 26 therewithin, as shown in differing levels of inflation, in FIGS. 10, 11 and 12. The pop-off waste gate valve 44 regulates the pressure within the intrauterine balloon 26 both initially and throughout the duration of its function within the uterus. Subsequent video microendoscope visualization of the developing implanted embryo may be accomplished five or seven days post embryo transfer through the same gas-tight rubber seal.

I claim:

1. A method for the emplacement of an embryo against an endometrium wall of a uterus, comprising the steps of:

placing an embryo onto a balloon;

inserting said balloon into a uterus;

inflating said balloon in the uterus, so as to expand said balloon with said embryo emplaced thereon, for application of said embryo against the endometrium and implantation within the uterus.

2. The method for the emplacement of an embryo against an endometrium wall of a uterus, as recited in claim 1, wherein the step of inserting further includes:

inserting said balloon over a hollow inserter tube.

3. The method for the emplacement of an embryo against an endometrium wall of a uterus, as recited in claim 2, including the step of:

directing a gas through said hollow inserter tube to inflate said balloon.

4. The method for the emplacement of an embryo against an endometrium wall of a uterus, as recited in claim 3, including the steps of:

arranging a pocket in said inserter tube; and emplacing a portion of said balloon in said pocket.

5. The method for the emplacement of an embryo against an endometrium wall of a uterus, as recited in claim 4, including the step of:

placing said embryo on said balloon in said pocket in said inserter tube.

6. The method for the emplacement of an embryo against an endometrium wall of a uterus, as recited in claim 5, including the step of:

placing a fiber optic device through said inserter tube, to permit visualization of said balloon therethrough.

7. The method for the emplacement of an embryo against an endometrium wall of a uterus, as recited in claim 5, including the step of:

placing an opening in a wall portion of said tube adjacent a distal end thereof, to permit said balloon to be inflated by gas pressure from said inserter tube.

8. The method for the emplacement of an embryo against an endometrium wall of a uterus, as recited in claim 4, including the step of:

folding a portion of said balloon over said pocket in said inserter tube, to permit said folded portion of said balloon to be a flap valve, keeping said embryo safe within said pocket until a pressurized inflation of said balloon effects displacement of said balloon and embryo from said pocket and against the endometrium wall of the uterus.

9. The method for the emplacement of an embryo against an endometrium wall of a uterus, as recited in claim 6, including the step of:

viewing said balloon and the embryo implanted against the endometrium.

10. The method for the emplacement of an embryo against an endometrium wall of a uterus, as recited in claim 8, including the step of:

arranging a valve in a stem portion of said balloon to regulate said pressurized inflation of said balloon.

11. The method for the emplacement of an embryo against an endometrium wall of a uterus, as recited in claim 10, including the step of:

occluding the entry of an undesired gas into the uterus by inflation of said balloon therewithin.

12. A method for the visualization of an embryo at an implantation site in a uterus, comprising the steps of:

placing the embryo onto a balloon;

directing a fiberoptic device into said balloon;

inserting said balloon into a uterus;

inflating said balloon by a fluid pressure when said balloon is in the uterus, so as to expand said balloon with said embryo placed thereon against the endometrium for implantation of said embryo in the uterus; and viewing said embryo through said fiberoptic device.

13. The method for the visualization of an embryo at an implantation site in a uterus, as recited in claim 12, including the step of:

placing said fiberoptic device into a tubular inserter; and wherein said step of inserting step further includes inserting said balloon into the uterus by said tubular inserter.

14. The method for the visualization of an embryo at an implantation site in a uterus, as recited in claim 13, including the step, of:

removing said tubular inserter to permit pressurization over a period of time of said balloon against the endometrium of the uterus.

15. The method for the visualization of an embryo at an implantation site in a uterus, as recited in claim 14, including the step, of:

placing a valve in a stem of said balloon to control said fluid pressure within said balloon as the embryo grows.

16. A method for the placement of an embryo at an optimal implantation site in a uterus, comprising the steps of:

placing the embryo onto a balloon;

inserting said balloon into a uterus; and inflating said balloon in the uterus, so as to expand said balloon with the embryo placed thereon and so as to apply the embryo against the endometrium for optimal implantation thereat to prevent a tubal positioning of the embryo.

17. The method for the placement of an embryo at an optimal implantation site in a uterus, as recited in claim 16, including the step of:

placing a fiberoptic device into said balloon; and viewing said embryo through said fiberoptic device.

18. The method for the placement of an embryo at an optimal implantation site in a uterus, as recited in claim 17, including the step of:

deflating said balloon as the embryo grows within the uterus.

19. A method to regulate multiple gestations within a uterus of a human female comprising the steps of:

placing an embryo onto a balloon;

inserting said balloon with the embryo thereon into a uterus; and inflating said balloon in the uterus, so as to expand said balloon with the embryo placed thereon and so as to apply the embryo against the endometrium for optimal implantation of the embryo in the uterus and to prevent emplacement of multiple embryos onto the endometrium of the uterus.

20. The method to regulate multiple gestations within a uterus of a human female, as recited in claim 19, wherein said step of inserting further includes:

inserting said balloon over a hollow inserter tube.

21. The method to regulate multiple gestations within a uterus of a human female, as recited in claim 20, including the step of:

directing a gas through said hollow inserter tube to inflate said balloon.

22. The method to regulate multiple gestations within a uterus of a human female, as recited in claim 21, including the steps of:

arranging a pocket in said inserter tube; and emplacing a portion of said balloon in said pocket.

23. The method to regulate multiple gestations within a uterus of a human female, as recited in claim 22, including the step of:

placing an embryo on said balloon in said pocket in said inserter tube.

24. The method to regulate multiple gestations within a uterus of a human female, as recited in claim 22, including the step of:

placing a fiber optic device through said inserter tube, to permit visualization of said balloon and embryo therethrough.

25. The method to regulate multiple gestations within a uterus of a human female, as recited in claim 24, including the step of:

placing an opening in a wall portion of said tube adjacent a distal end thereof, to permit said balloon to be inflated by gas pressure from said tube.

26. An apparatus for the emplacement of an embryo against an endometrium wall of a uterus, comprising:

a balloon having an outer surface for the receipt of an embryo thereon;

a hollow inserter tube having a proximal and a distal end; an optical fiber viewing device movably arranged within said hollow inserter tube;

said balloon arranged on said distal end of said inserter tube; and a cavity arranged adjacent said distal end of said inserter tube, for receipt of a portion of said balloon and the embryo during insertion of said balloon on said inserter tube into a uterus.

27. The apparatus for the emplacement of an embryo against an endometrium wall of a uterus, as recited in claim 26, including:

an inflation conduit within said inserter tube to permit inflation of said balloon inside a uterus.

28. The apparatus for the emplacement of an embryo against an endometrium wall of a uterus, as recited in claim 27, including:

a flap valve arranged over said cavity holding said embryo, to permit safe delivery of the embryo in said cavity during insertion of said inserter tube, said balloon and the embryo into the uterus.

29. The apparatus for the emplacement of an embryo against an endometrium wall of a uterus, as recited in claim 27, including:

a regulator valve at a proximal stem end of said balloon to permit regulation of pressure of gas within said balloon during implantation of the embryo onto the endometrium in the uterus.

30. The apparatus for the emplacement of an embryo against an endometrium wall of a uterus, as recited in claim 28, including:

a frangible means arranged on said distal end of said inserter tube, to permit said optical fiber viewing device to be pushed therepast, to permit said viewing device to view said balloon and the embryo after said balloon has been inflated, and the embryo has been implanted onto the endometrium wall of the uterus.

* * * * *